(12) United States Patent
Olschimke et al.

(10) Patent No.: US 8,308,850 B2
(45) Date of Patent: Nov. 13, 2012

(54) METHOD FOR SEPARATING GAS

(75) Inventors: Jens Olschimke, Hannover (DE); Saskia Braukmüller, Sarstedt (DE); Carsten Brosch, Seelze (DE)

(73) Assignee: Solvay Fluor GmbH, Hannover (DE)

( * ) Notice: Subject to any disclaimer, the term of this patent is extended or adjusted under 35 U.S.C. 154(b) by 870 days.

(21) Appl. No.: 11/666,581

(22) PCT Filed: Oct. 20, 2005

(86) PCT No.: PCT/EP2005/011267
§ 371 (c)(1),
(2), (4) Date: Mar. 6, 2009

(87) PCT Pub. No.: WO2006/045518
PCT Pub. Date: May 4, 2006

(65) Prior Publication Data
US 2009/0211449 A1    Aug. 27, 2009

(30) Foreign Application Priority Data

Oct. 27, 2004  (EP) ..................... 04025509
Dec. 22, 2004  (DE) .......... 10 2004 061 780

(51) Int. Cl.
*B01D 53/14* (2006.01)
(52) U.S. Cl. ..................... 95/233; 423/240 R
(58) Field of Classification Search .......... 95/233, 95/46, 241, 156; 423/240 R, 210; 96/108, 96/155, 243
See application file for complete search history.

(56) References Cited

U.S. PATENT DOCUMENTS

| | | | |
|---|---|---|---|
| 6,489,510 B1 | 12/2002 | Braun et al. | |
| 6,579,343 B2 * | 6/2003 | Brennecke et al. | 95/51 |
| 7,208,605 B2 * | 4/2007 | Davis, Jr. | 548/110 |
| 7,396,381 B2 * | 7/2008 | Graham et al. | 95/46 |
| 7,404,845 B2 * | 7/2008 | Tempel et al. | 95/46 |
| 7,435,318 B2 * | 10/2008 | Arlt et al. | 203/14 |
| 2002/0189444 A1 | 12/2002 | Brennecke et al. | |
| 2003/0204041 A1 | 10/2003 | Laas et al. | |
| 2006/0049102 A1 * | 3/2006 | Miller et al. | 210/500.27 |

FOREIGN PATENT DOCUMENTS

| | | |
|---|---|---|
| DE | 10114565 A1 | 9/2002 |
| EP | 1394109 A1 | 3/2004 |
| WO | WO/02/074718 A2 | 9/2002 |
| WO | WO/2005/007657 A2 | 1/2005 |
| WO | WO/2005/085129 A2 | 9/2005 |
| WO | WO/2007/125065 A1 | 11/2007 |

OTHER PUBLICATIONS

Wasserscheid et al., "Ionic Liquids—New "Solutions" for Transition Metal Catalysis", *Angew. Chem. Int. Ed.*, vol. 39, pp. 3772-3789 (2000).

Yoshizawa et al "Novel Polymer Electrolytes Prepared by Copolymerization of Ionic Liquid Monomers", *Polymers for Advanced Technologies*, vol. 13, pp. 589-594 (2002).

Strauss, "The Search for Larger and More Weakly Coordinating Anions", American Chemical Society, *Chem. Rev.*, vol. 93, pp. 927-942 (1993).

Reichardt, "Empirical Parameters of Solvent Polarity from Spectroscopic Measurements", *Solvent Effects in Organic Chemistry*, pp. 237-250 (1979).

"Technical Summaries on Ionic Liquids in Chemical Processing", www.chemicalvision2020.org/pdfs/tech_summary.pdf, pp. 1-30 (2003).

* cited by examiner

*Primary Examiner* — Duane Smith
*Assistant Examiner* — Ives Wu
(74) *Attorney, Agent, or Firm* — Connolly Bove Lodge & Hutz LLP

(57) ABSTRACT

Gas mixtures containing HF, HCl or HBr and other constituents, in particular gas mixtures containing carboxylic acid fluorides, $C(O)F_2$ or phosphorus pentafluoride and HCl and possibly HF, can be fractionated by means of ionic liquids.

24 Claims, No Drawings

METHOD FOR SEPARATING GAS

RELATED APPLICATIONS

This application is a national stage application (under 35 U.S.C. §371) of PCT/EP2005/011267 filed Oct. 20, 2005, which claims benefit of European application 04025509.3 filed Oct. 27, 2004 and German application 10 2004 061 780.5 filed Dec. 22, 2004.

The invention relates to a process for separating mixtures containing HCl, HF and/or HBr and other constituents, in particular mixtures which contain $C(O)F_2$, phosphorus pentafluoride or particular acid fluorides and HCl and possibly HF.

Gaseous organic acid fluorides such as $CF_3C(O)F$ or $CHF_2C(O)F$ are starting materials for fluorine-containing organic compounds, for example for fluorovinyl ethers which are in turn comonomers for resins or elastomers. $CF_3C(O)F$ has been proposed as a pesticide. Acid fluorides can, as a result of the method of preparation, contain HCl or HBr, sometimes also HF.

Phosphorus pentafluoride is an intermediate in the preparation of electrolyte salts for lithium ion batteries. It can, for example, be reacted with lithium fluoride to form lithium hexafluorophosphate. The phosphorus pentafluoride can be prepared from phosphorus pentachloride or phosphorus trichloride and chlorine and also hydrogen fluoride. In this reaction, HCl is formed and has to be separated off from the phosphorus pentafluoride.

Carbonyl fluoride has been proposed as new etching gas in semiconductor technology and for cleaning CVD reactors. The European patent application 04005421.5 (corresponds to WO05/085129) describes a photochemical process for preparing $C(O)F_2$ from $CHClF_2$. The process described there provides the preparation of $C(O)F_2$ by photooxidation of $CHClF_2$ by means of oxygen. Here, light which does not have a single wavelength but instead has a spectral range covering at least 50 nm (i.e. the light having the shortest wavelength and the light having the longest wavelength are at least 50 nm apart) is radiated in.

In the process described there, the pressure in the reactor preferably corresponds to at least ambient pressure, i.e. 1 bar (abs.). It can also be above this. The pressure is preferably in the range from 1 bar (abs.) to 11 bar (abs.). The temperature is preferably in the range from 20 to 300° C., particularly preferably in the range from 30 to 300° C. and in particular in the range from 30 to 90° C. The pressure and temperature conditions are advantageously selected so that the reaction mixture remains gaseous.

The process described there is very particularly preferably carried out without applied pressure. The term "without applied pressure" there means that no additional pressure in addition to ambient pressure (i.e. about 1 bar), the transport pressure of the oxygen gas (or the oxygen-containing gas since, for example, air or oxygen/inert gas mixtures can be used) and any chlorine used and any pressure generated by hydrogen chloride gas formed in the reaction is applied to the reaction mixture. The total pressure in the reactor is then advantageously less than 2 bar absolute, depending on the transport pressure even less than 1.5 bar absolute, but greater than ambient pressure.

The process can be carried out batchwise or preferably continuously. The preferred procedure is to feed starting material (the appropriate feedstock, oxygen or an oxygen-containing gas such as air or pure oxygen and if appropriate chlorine) continuously into a flow-through apparatus and to take off reaction product continuously in an amount corresponding to the amount fed in. The average residence time in the reaction vessel is advantageously from 0.01 to 30 minutes, preferably from 0.1 to 3 minutes, particularly preferably from 0.3 to 1.5 minutes. The optimal average residence time, which depends, inter alia, on the type of lamps, the radiative power of the lamps and on the geometric parameters of the irradiation apparatus, can be determined by means of simple tests and analysis of the product stream, for example by gas chromatography. It can also be advantageous to generate good turbulence in the reaction mixture, for example by means of suitable internals in the reactor. The optimal residence time in the case of a batch process can be determined in the same way.

One embodiment provides the photooxidation in the absence of chlorine or other free-radical initiators or activators. For example, the irradiation can be performed through fused silica; other components of the reactor which are not located between the light source and the reaction mixture can naturally be made of any materials, e.g. borosilicate glass which filters particular components of the radiation (see below). Suitable lamps are customary lamps which emit, for example, radiation in the range from 250 to 400 nm or even up to 600 nm (the spectrum can also go beyond the upper or lower limit).

A further, particularly preferred embodiment in that European patent application provides irradiation with light having a wavelength of $\geq 280$ nm in the presence of elemental chlorine, with a maximum of 0.6 part by weight of elemental chlorine per part by weight of $CHClF_2$ being present in the reaction mixture. Preference is given to using from 1 to 50 mol % of chlorine, more preferably from 5 to 20 mol % of elemental chlorine, per mole of $CHClF_2$.

The conversion, yield and selectivity are particularly high in the process described there if the reaction is carried out in the presence of elemental chlorine and activating irradiation with light having a wavelength $\lambda \geq 280$ nm is employed. Frequencies having a wavelength below 280 nm are then essentially masked out of the frequency spectrum. This can be effected by using irradiation lamps which emit only light having a wavelength above or at 280 nm and/or by using means which mask the appropriate frequencies out of the emitted light. For example, irradiation can be carried out through glass which is transparent only to light having a wavelength of 280 nm or above, i.e. filters out the shorter wavelength components of the radiation. Borosilicate glasses, for example, are particularly useful for this purpose. Suitable glasses contain, for example, from 7 to 13% of $B_2O_3$, from 70 to 80% of $SiO_2$, also from 2 to 7% of $Al_2O_3$ and from 4 to 8% of $Na_2O+K_2O$ and also from 0 to 5% of alkaline earth metal oxides (in each case in % by weight). Known brands of borosilicate glasses are Duran, Pyrex and Solidex.

The molar ratio of the starting material to oxygen can vary within a wide range in the process described in the above mentioned European patent application, but it is advantageous to use at least 0.4 mol of oxygen per mole of starting compound. Particularly good results are achieved when the molar ratio of the starting compound to oxygen is in the range from 1:0.4 to 1:1, in particular from 1:0.4 to 1:0.6. The oxygen can, as stated, be used in the form of air. The oxygen is preferably used in the form of an $O_2$/inert gas mixture, but in particular as pure oxygen. With regard to the product purity, it is desirable for very little water to be present in the reaction (for example less than 30 ppm). If desired, the reactants can be freed of entrained water in a known manner, e.g. by means of molecular sieves. Separation of $C(O)F_2$ and HCl can be achieved, for example, by pressure distillation.

However, owing to the fact that the boiling point of $C(O)F_2$ and HCl are close together, separation by distillation is costly.

Mixtures containing HF can, for example, be the result of a fluorination reaction with hydrogen fluoride. Thus, carboxylic acid fluorides can be prepared by reaction of carboxylic acid chlorides and HF or photochemically (U.S. Pat. No. 6,489,510). These mixtures usually also contain HCl.

In addition to the above-described problems of separating HCl/carboxylic acid fluoride, HF/carboxylic acid fluoride, HF/HCl/carboxylic acid fluoride, HCl/PF$_5$ or HCl/C(O)F$_2$, it can generally be desirable to separate HF, HCl or HBr off from gas mixtures containing HF, HCl or HBr together with other constituents or fractionate these gas mixtures so as to give gas mixtures or pure gases which are depleted in HF, HCl or HBr or are enriched in the other component or components.

The European patent application EP-A 1 394 109 describes a process for separating HF and similar acids from acid fluorides. As deacidifying agent, a heteroaromatic compound which has a boiling point of at least 50° C. and has nitrogen as heteroatom or heteroatoms is recommended. As indicated in the description of the patent application mentioned, the heteroaromatic compound can be an amine (amines have an appreciable vapour pressure even at temperatures below 100° C.) such as imidazole or pyridine or an appropriate ion-exchange resin having amino groups such as pyridine or imidazole groups. Examples of such polymers are polyvinyl (4-pyridine) and polyvinyl(2-pyridine). Ionic liquids are not used.

The international patent application WO 02/074718 discloses ionic liquids as selective additives for the separation of close-boiling or azeotropic mixtures. These mixtures are liquids or condensed gases, i.e. the separation is a liquid-liquid separation. As mixtures to be separated, mention is made of mixtures of water with amines, tetrahydrofuran, formic acid, alcohols, acetates, acrylates, acetic acid, mixtures of acetone and methanol or close-boiling mixtures such as C4-, C3-hydrocarbons or alkanes/alkenes. The mixtures are thus purely organic mixtures, often of compounds having at least 3 carbon atoms, or mixtures containing water.

The US patent application 2004/0035293 discloses ionic liquids which have a group having Brönsted-acid properties, e.g. a sulphonic acid group. Such ionic liquids can be used for separating off gases, e.g. for separating off or transferring CO$_2$ or COS, for separating off alkenes, alkynes or CO or for catalysis.

The US patent application 2002/0189444 (=U.S. Pat. No. 6,579,343) discloses a process for putrifying gases by means of ionic liquids. For example, water, CO$_2$, oxygen and the like can be separated off from gas mixtures. In this way, natural gas, air or oxygen can be purified.

It is therefore an object of the present invention to provide a process which is simple to carry out and by means of which HF, HCl or HBr can be separated off from gas mixtures so as to give a gas mixture which is depleted in HF, HCl or HBr or is enriched in the other component or components.

A preferred object of the present invention is to provide a process by means of which C(O)F$_2$, phosphorus pentafluoride or carboxylic acid fluoride depleted in HCl can be obtained from mixtures containing C(O)F$_2$ or phosphorus pentafluoride and HCl or by means of which the C(O)F$_2$ or phosphorus pentafluoride can be obtained in enriched form from these mixtures. This object is achieved by the process of the present invention.

In the broadest sense, the present object is achieved by the process of the invention for separating HF, HCl or HBr from gas mixtures containing HF, HCl or HBr and one or more other gaseous constituents, wherein these gas mixtures are contacted with one or more ionic liquids which sorb HF, HCl or HBr or at least one of the other constituents of the gas mixture to a differing degree. In no case is water added and the ionic liquid is preferably essentially water-free (e.g. has a water content of less than 0.1% by weight), so that hydrolysis of the fluorides can occur to only a small extent, if at all. Ionic liquids are added at the beginning in the process of the present invention. The compounds present as other components in the gas mixtures to be treated are compounds which are gases under standard conditions (25° C., 1 bar abs.), e.g. trifluoroacetyl fluoride, trifluoroacetyl fluoride, PF$_5$, C(O)F$_2$, etc.

Water present in the ionic liquid is consumed by reaction with the hydrolysis-sensitive constituents of the gas mixture (carbonyl fluoride, acid fluoride or PF$_5$) when the gas mixture to be fractionated is passed through it. The components formed are mostly volatile and easy to remove from the ionic liquid.

The process is particularly suitable for separating off HCl and is described further in this regard.

The process is suitable, for example, for gas mixtures which contain HCl and carboxylic acid chlorides which are gaseous under standard conditions, e.g. trifluoroacetyl chloride (TFAC) or difluoroacetyl chloride (DFAC). It can also be employed for separating HCl from carboxylic acid fluorides which are gaseous under standard conditions, in particular from difluoroacetyl fluoride, trifluoroacetyl fluoride, C$_2$F$_5$C(O)F or CH$_3$C(O)F. It can also be applied to gas mixtures containing HBr and other constituents. It is preferably used for purifying carbonyl fluoride or carboxylic acid chlorides or carboxylic acid fluorides having not more than 2 carbon atoms. If HF is present, this is likewise separated off.

While many processes according to the prior art provide a separation of liquid components or condensed gases, in the process of the present invention preference is given to fractionating a gas mixture which is contacted in gaseous form with the ionic liquids, i.e. it is not brought into contact in the condensed state with the ionic liquid.

The abovementioned particular object of treating gas mixtures containing C(O)F$_2$ and HCl, treating gas mixtures containing carboxylic acid fluoride and HF and/or HCl or treating gas mixtures containing phosphorus pentafluoride and HCl is achieved by the process of the invention for isolating C(O)F$_2$, carboxylic acid fluoride or phosphorus pentafluoride which is depleted in HF or HCl or HF and HCl or enriched in C(O)F$_2$, carboxylic acid fluoride or phosphorus pentafluoride. This preferred process provides for these mixtures to be contacted with an ionic liquid which sorbs C(O)F$_2$, carboxylic acid fluoride or phosphorus pentafluoride to a differing degree to that with which it sorbs HF, HCl or HBr. Although it is possible to select ionic liquids which allow HCl, HF or HBr to pass and sorb the other constituents, it is usually the case that HCl, HF or HBr is sorbed more strongly by ionic liquids and C(O)F$_2$, carboxylic acid fluoride or phosphorus pentafluoride depleted in HCl, HF and/or HBr passes the ionic liquid and can be isolated or the gas or gas mixture obtained is enriched in C(O)F$_2$, carboxylic acid fluoride or phosphorus pentafluoride. The invention is explained further for its preferred application to mixtures containing HCl and C(O)F$_2$.

For the purposes of the present invention, ionic liquids are as defined by Wasserscheid and Keim in Angewandte Chemie 2000, 112, 3926-3945. Ionic liquids can, for example, be used as solvents. As stated in the documents cited, ionic liquids are salts which melt at relatively low temperatures and have a nonmolecular, ionic character. They are liquid even at relatively low temperatures, e.g. <100° C., and have a relatively low viscosity. They have very good solvent capabilities for a large number of organic, inorganic and polymeric substances.

Furthermore, ionic liquids are generally nonflammable, noncorrosive and have a low viscosity and display an imperceptible vapour pressure.

The ions of the ionic liquids which can be used in the present invention can have one or more positive or negative charges, with ions having one positive charge and one negative charge being preferred.

Ionic liquids which are suitable for the separation of mixtures of substances are described in WO 02/074718. They are based on ionic liquids which have ammonium, guanidinium or phosphonium ions as cations. In general, the ionic liquids are selected so that they undergo no chemical reaction leading to decomposition with a component of the gas mixture to be fractionated. This can easily be ensured by means of simple tests. If constituents which are sensitive to moisture are present in the gas mixture, it is advantageous for moisture to be largely excluded, e.g. by means of desiccants in the reactor, by flushing with dry inert gas or the like. The same applies to any sensitivity to oxygen. It is also possible to utilize further ionic liquids, e.g. those having guanidinium cations.

For the purposes of the present invention, preference is given to cations which contain nitrogen.

Suitable cations and anions are described in more detail below; it will here be clear to a person skilled in the art that the respective cation/anion pairs have to give a product which has to be liquid at a temperature of not more than 100° C. in order to give a useable ionic liquid. Ionic liquids or mixtures of ionic liquids which are liquid at ambient temperature (about 20° C.) are particularly advantageous.

Phosphorus-containing cations, in particular phosphonium cations having four identical or different alkyl groups, e.g. butyl, octyl or phenyl radicals, have been mentioned in the abovementioned publication by Wasserscheid and Keim.

Preference is given to nitrogen-containing cations; the invention will be described in more detail for this embodiment.

In principle, it is possible to use all known cations which have at least one organic substituent on the ammonium cation. In general, these are primary, secondary, tertiary and quaternary ammonium cations. The substituents can, for example, be linear or branched alkyl groups, for example alkyl groups having from 1 to 12 carbon atoms. It is possible for identical or different alkyl substituents to be present on the nitrogen atom. The substituents can also be aromatic radicals, for example the phenyl radical which may, if desired, bear one or more substituents, for example one or more C1-C3 groups. Arylalkyl substituents, for example the benzyl radical, are also possible. Guanidinium cations and isouronium cations are also suitable cations (such compounds are obtainable from Merck Darmstadt). The substituents on the nitrogen can be hydrogen, linear or branched alkyl groups or aryl groups. The substituents on the nitrogen, oxygen and sulphur atoms can be linear or branched alkyl groups or aryl groups. Hydrogen can also be present as substituent on the nitrogen.

It is also possible to utilize cyclic saturated ammonium cations, for example those mentioned in the German published application DE 101 14 565, substituted or unsubstituted monocyclic or bicyclic saturated ammonium cations, for example piperidinium or hydroxyl-substituted piperidinium. The cations of bicyclic amines, in particular those of 1,5-diazabicyclo[4.3.0]non-5-ene and 1,8-diazabicyclo[5.4.0]undec-7-ene, and also amino-substituted cyclic amines such as dialkylaminopiperidine and dialkylaminopiperazine (alkyl is C1 to C4) mentioned in this publication can also be used in the form of the cations.

Suitable cations also include heterocyclic compounds which contain at least one nitrogen atom and, if desired, an oxygen or sulphur atom and have been mentioned in the abovementioned WO 02/074718 on pages 4 to 6. These are cations based on the structure of pyridine, pyridazine, pyrimidine, pyrazine, imidazole, 1H-pyrazole, 3H-pyrazole, 4H-pyrazole, 1-pyrazoline, 2-pyrazoline, 3-pyrazoline, 1-imidazoline, 2-imidazoline, 4-imidazoline, thiazole, oxazole, 1,2,4-triazole (positive charge on the nitrogen atom in the 2 or 4 position), 1,2,3-triazole (positive charge on the nitrogen atom in the 2 or 3 position) and pyrrolidine. Details of the substituents may be found in WO 02/074718 on pages 6 to 13. Cations of N-alkylisoquinoline, alkyltriazolium, N-alkylimidazoline can likewise be employed. These structures can be substituted by hydrogen. One or more hydrogen atoms can also be replaced, for example by alkyl groups having from 1 to 18 carbon atoms (C2-C18-alkyl groups can also contain one or more oxygen or sulphur atoms or imino groups in the chain), by C6-C12-aryl, C5-C12-cycloalkyl or a five- or six-membered, oxygen-, nitrogen- or sulphur-containing heterocyclic radical. Two of the substituents can also form an unsaturated or saturated or aromatic ring which may be interrupted by one or more oxygen or sulphur atoms or imino groups. The substituents mentioned may in turn be substituted by functional groups, aryl, alkyl, aryloxy, alkyloxy, halogen, heteroatoms and/or heterocycles.

A substituent on the nitrogen atom which bears the positive charge can also be, for example, C1-C18-alkylcarbonyl, C1-C18-alkyloxycarbonyl, C5-C12-cycloalkylcarbonyl or C6-C12-arylcarbonyl; the substituents, too, may in turn be substituted by functional groups, aryl, alkyl, aryloxy, alkyloxy, halogen, heteroatoms and/or heterocycles.

Cations of such heterocycles having five-membered or six-membered rings are preferred in the process of the present invention.

Particularly well-suited cations are imidazolium, imidazolinium, pyrazolium, oxatriazolium, thiatriazolium, pyridinium, pyradizinium, pyrimidinium or pyrazinium cations. Here, the carbon atoms can preferably be substituted by hydrogen, C1-C12-alkyl or C2-C12-alkyl substituted by a hydroxy or CN group. The nitrogen atom bearing the positive charge is preferably substituted by acetyl, methyl, ethyl, propyl or n-butyl. It can, if appropriate, as in the case of any further nitrogen atoms present in the ring, also be substituted by hydrogen or C1-C12-alkyl groups. C1-C12-alkyl is preferably methyl, ethyl, propyl or n-butyl.

It is also possible to use oligomers and polymers containing the above-described cations (see, for example, M. Yoshizawa, W. Ogihara and H. Ohno, Polym. Adv. Technol. 13, 589-594, 2002). However, monomeric cations are preferred for the purposes of the present invention.

Very particularly preferred cations are imidazolium cations which are substituted by one, two or three substituents each having 1-24 carbon atoms; here, the substituents may in turn be substituted by, for example, aryl groups. Particular preference is given to 1,3-dimethylimidazolium, 1-ethyl-3-methylimidazolium, 1-propyl-3-methylimidazolium, 1-butyl-3-methylimidazolium, 1-pentyl-3-methylimidazolium, 1-hexyl-3-methylimidazolium, 1-heptyl-3-methylimidazolium, 1-octyl-3-methylimidazolium, 1-nonyl-3-methylimidazolium, 1-decyl-3-methylimidazolium, 1-undecyl-3-methylimidazolium, 1-dodecyl-3-methyl-imidazolium, 1-benzyl-3-methylimidazolium, 1-butyl-2,3-dimethylimidazolium. Ionic liquids having 1,3-dimethylimidazolium, 1-ethyl-3-methylimidazolium ("EMIM"), 1-propyl-3-methylimidazolium and 1-n-butyl-3-methylimidazolium ("BMIM") as cation are very suitable.

Particularly suitable anions are anions which can form hydrogen bonds. Strongly coordinating anions such as alkylsulphates or arylsulphates are more suitable than weakly coordinating anions such as trifluoromethanesulphonate and in particular hexafluorophosphate or tetrafluoroborate because they often give good purification results even in a single-stage procedure. Further suitable anions are halides but in particular the anions of monobasic or polybasic oxo acids or their derivatives such as esters or amides, e.g. sulphonates or sulphonamides. Further well-suited ionic liquids are those having the following anions: alkylcarboxylates having a total of from 2 to 8 carbon atoms, for example acetate; alkylcarboxylates substituted by halogen, in particular fluorine, e.g. trifluoroacetate; Sulphate; hydrogensulphate; phosphate; hydrogenphosphate; dihydrogenphosphate; alkylsulphate having a C1-C12-alkyl radical which may be linear or branched, with specific anions being, for example, methylsulphate, ethylsulphate, n-propylsulphate, n-butylsulphate through to n-octylsulphate; alkylphosphate and dialkylphosphate having one or two C1-C12-alkyl radicals, e.g. methylphosphate, dimethylphosphate, ethylphosphate, diethylphosphate, n-propylphosphate, di-n-propylphosphate, n-butylphosphate, di-n-butylphosphate; C1-C12-alkylsulphonate, preferably C1-C4-alkylsulphonate, e.g. methyl-, ethyl-, n-propyl-, n-butylsulphate; sulphonate having a C1-C12-alkyl group substituted by one or more halogen atoms, preferably fluorine, e.g. trifluoromethylsulphonate (triflate); arylsulphonate, e.g. tosylate; phosphonate having a C1-C12-alkyl group which is bound directly to the phosphorus, e.g. methylphosphonate, ethylphosphonate, n-propylphosphonate, n-butyl-phosphonate; phosphonate having a C1-C12-alkyl group which is substituted by one or more halogen atoms, preferably fluorine, and is bound directly to the phosphorus, e.g. trifluoromethylphosphonate; esters of the abovementioned phosphonates having a C1-C12-alkyl group which may, if desired, also be substituted by one or more halogen atoms, preferably fluorine atoms; imides of bis(C1-C12-alkylsulphonate), where the alkyl groups may, if desired, be substituted by one or more halogen atoms, preferably fluorine, e.g. bis(trifluoromethylsulphonyl)imide.

Preferred anions are C1-C12-alkylsulphates, particularly preferably C1-C4-alkylsulphates, in particular methylsulphate and ethylsulphate, and also, as indicated below, triflate and tosylate and also mixtures thereof.

Without attempting to give a scientific explanation, the results indicate that it is not so much the polarity of an ionic liquid but rather the presence of strongly coordinating anions in an ionic liquid, e.g. methylsulphate and ethylsulphate, which influence the uptake of HCl or HBr. Weakly coordinating or "noncoordinating" anions (S. H. Strauss, Chem. Rev. 1993, 93, 927-942), e.g. $SO_3CF_3$ and in particular $PF_6$ and $BF_4$, in which the negative charge is strongly delocalized do not display any particularly strong HCl or HBr absorption effect. On the other hand, ionic liquids having the $SO_3CF_3$ anion have the process engineering advantage that they are very stable towards HCl and other constituents of the gas mixture. A somewhat lower affinity towards HCl is balanced here by a high stability. If desired, the absorption process by means of ionic liquids having $SO_3CF_3$ as anion is carried out two or more times until the desired removal of HCl has been achieved. Further anions which have been found to be very useful are the three isomeric tosylate anions (o-toluenesulphonate, m-toluenesulphonate and in particular p-toluenesulphonate). Ionic liquids having the tosylate anion can be present in liquid or solid form at room temperature. Ionic liquids having the tosylate anion can, if desired, be used in the form of mixtures with other ionic liquids which lower the melting point (this naturally also applies to the other ionic liquids which have a melting point which is higher than desired). Ionic liquids which contain an anion mixture of triflate and tosylate or preferably consist thereof, e.g. in a molar ratio of from 0.1:1 to 10:1, preferably from 3:7 to 7:3, are a good compromise between effectiveness of the depletion and stability and have a sufficiently low melting point, in the range from 0 to 60° C. Consisting of the mixtures mentioned means that no ionic liquids having anions other than triflate and tosylate are present.

Preferred ionic liquids are often ones having a $E_T(30)$ value of more than 20, preferably more than 30, in particular more than 40. This value is a measure of the polarity, see Reichardt, Solvent Effects in Organic Chemistry, Weinheim VCH, 1979, XI (Monographs in Modern Chemistry; 3) page 241.

In the process of the invention, it is possible to use ionic liquids which contain only one compound. It is also possible to use mixtures of two, three or more different ionic liquids. In this way, it is possible to influence, for example, the separation properties, for example the polarity or the affinity towards a compound to be separated off; or it is possible to influence the viscosity or the temperature at which the mixture becomes solid. the latter is exploited in mixtures of 1-ethyl-3-methylimidazolium triflate and 1-ethyl-3-methylimidazolium tosylate.

The contact between the gas mixture to be treated and the ionic liquid can be brought about by methods customary in gas-liquid operations. For example, the gas mixture to be treated can be passed through the ionic liquid; suitable nozzles, frits or mixing devices enable the contact area to be increased. It is possible, for example, to effect contact in a bubble column. If desired, the ionic liquid can also be immobilized, e.g. on a support, e.g. a ceramic material, or incorporated in a polymer; this embodiment is less preferred.

The pressure can vary within a wide range; it can, for example, be from ambient pressure up to 10 bar (absolute) or even higher. In process engineering terms, it is simplest to carry out the contacting at ambient pressure or a slight overpressure in order to press the gas mixture into the ionic liquid.

The temperature can likewise be varied within a wide range. The temperature is advantageously selected so that the viscosity is in the desired range. A temperature range which extends essentially from the decomposition temperature to the solidification temperature, preferably from 100° C. down to the solidification temperature, of the ionic liquid or the mixture of ionic liquids is possible. The temperature of the ionic liquid on contact with the mixture to be separated is preferably in the range from the solidification temperature of the ionic liquid, e.g. above 10° C., up to 80° C. As stated, a range from the solidification temperature to the decomposition temperature is in principle possible.

Ideally, HCl or HF is retained in the ionic liquid and $C(O)F_2$, $PF_5$ or acid fluoride passes the ionic liquid. In the case of a sufficient purity, the gases can be condensed and passed onto the respective use. In the case of some separation problems, further, constituents which likewise pass the ionic liquid can be present in the gas mixture. In the case of gas mixtures of $C(O)F_2$ and HCl from the photochemical oxidation of $CHClF_2$, it is possible for, for example, starting material also to be present. The constituents of the gas mixture which are not retained in the ionic liquid can be separated off in a customary way, e.g. by fractional distillation or condensation, before passage through the ionic liquid. As an alternative, they can be left in the gas mixture to be treated and be separated off after contact with the ionic liquid. An example is a fractional condensation or a condensation which may be followed, if desired, by a low-temperature distillation.

The constituents retained in the ionic liquid can be recovered from this physically in a reconditioning, e.g. by application of a vacuum, heating, passing through of inert gases or the like, if desired also by means of a combination of two or more such physical measures, e.g. increasing the temperature and applying a vacuum. The separation of the constituents of the gas mixture retained in the ionic liquid from the ionic liquid simultaneously regenerates the ionic liquid which is then available for renewed use. The desorption temperature is preferably not higher than 100° C., but can go Lip to below the decomposition temperature of the ionic liquid. In the case of application of a vacuum, 1 mbar is a limit which is often preferred for technical reasons. However, there are no objections to working at a lower pressure, e.g. $10^{-3}$ mbar, as successful experiments have shown. Desorption occurs very quickly (e.g. within from 1 to 2 hours) even at temperatures at or below 100° C. down to preferably 40° C. In contrast, the removal of the sorbed constituents as described in EP-A 1 394 109 requires heating at 150° C. and above for many hours.

In the case of desorption by changing the pressure, it is critical that the desorption is carried out at a pressure which is lower than the pressure on loading. If the gas mixture and the ionic liquid are contacted at superatmospheric pressure, e.g. at 5 bar (abs.) or more, the subsequent desorption can be effected at a pressure which is at or slightly above ambient pressure, e.g. at 1 or 1.5 bar (abs.). Desorption can naturally also be carried out at subatmospheric pressure and, if desired, elevated temperature to complete the reconditioning of the ionic liquid.

The invention further provides mixtures of ionic liquids containing the triflate and tosylate ion. Preference is given to mixtures in which the molar ratio of the ionic liquids containing the tosylate anion to those containing the triflate anion is from 0.1:10 to 10:0.1, preferably from 3:7 to 7:3. Tosylate is o-tosylate, m-tosylate, preferably p-tosylate.

Particular preference is given to mixtures of ionic liquids whose cations are different or preferably identical and belong to the class of imidazolium, imidazolinium, pyrazolium, oxatriazolium, thiatriazolium, pyridinium, pyradizinium, pyrimidinium or pyrazinium compounds and are, in particular, selected from among 1,3-dimethylimidazolium, 1-ethyl-3-methylimidazolium ("EMIM"), 1-propyl-3-methylimidazolium and 1-n-butyl-3-methylimidazolium ("BMIM").

In the mixtures of the invention, the proportion of ionic liquids having the triflate and tosylate anions is preferably at least 75% by eight of the total amount of ionic liquids. The balance to 100% by weight is made up by ionic liquids having other anions, e.g. the ethylsulphate anion. The proportion of ionic liquids having the triflate and tosylate anions is preferably at least 90% by weight, very particularly preferably 100% by weight. Especially preferred mixtures comprise EMIM triflate and EMIM tosylate or consist of the two components mentioned.

The process of the invention relates to a new separation problem which was not known in the prior art. It differs from known processes in that inorganic constituents (HCl, HBr, HF) are separated off or participate and in that it is not amines but instead ionic liquids which are used for the separation. It has the advantage that HCl, HF and HBr can be separated off in a simple way from other hydrolysis-sensitive constituents of a mixture, e.g. gaseous carboxylic acid chlorides and carboxylic acid fluorides, in particular from phosphorus pentafluoride or $C(O)F_2$. The ability to separate HCl from mixtures with $C(O)F_2$, which are obtained as a result of the method of production, is particularly advantageous. A significantly better degree of separation than, for example, in the publications U.S. Pat. No. 3,253,029 and U.S. Pat. No. 4,092,403, where acetonitrile is used as separating agent, is achieved here. Furthermore, the reconditioning of an ionic liquid has significant advantages over the recycling of an organic solvent such as acetonitrile or a hydrochloride of an amine. It is also possible to treat mixtures which originate from fluorination reactions of phosphorus-chlorine compounds with HF, in particular from the preparation of $PF_5$ from phosphorus(III) chlorides or phosphorus(V) chlorides and HF and also, if appropriate, $Cl_2$ or $F_2$.

The following examples illustrate the invention % without restricting its scope.

General

In the following examples, use was in some cases made of test mixtures which were prepared for the experiments and contained only two constituents to be separated from one another. For other examples, mixtures originating from photooxidation experiments and containing not only the constituents $C(O)F_2$ and HCl to be separated but also further components, in particular the starting compound $CHClF_2$, were used. The latter compound passes the ionic liquid together with the carbonyl fluoride. The further purification of the resulting mixtures can be effected by distillation—the further components are separated off in this way. As an alternative, a purification, e.g. with distillation of the reaction mixture containing further components, can first be carried out in order to separate off the reaction components beforehand; the resulting gas mixture then contains only carbonyl fluoride and HCl which are then separated by means of the ionic liquid.

In the experiments, tosylate is always p-tosylate.

EXAMPLE 1

Separation of HCl from a Mixture with $C(O)F_2$ 1.1. Use of 1-ethyl-3-methylimidazolium ethylsulphate at Room Temperature A $C(O)F_2$/HCl gas mixture was prepared by photooxidation of $CHF_2Cl$ using the process of the abovementioned as yet unpublished European patent application 04 00 5421.5. A crude gas mixture having the composition 45% of $C(O)F_2$, 34% of HCl, 6% of $O_2$ and further reaction components (starting materials, etc.) was passed at a flow rate of 0.8 mol/h and slightly elevated pressure through a wash bottle containing 115 g (0.49 mol) of 1-ethyl-3-methylimidazolium ethylsulphate ("EMIM ethylsulphiate"). To obtain hydrolysis-sensitive components (e.g. $C(O)F_2$) of a gas mixture, it is advantageous to exclude or minimize moisture in the apparatus and in the ionic liquid. This was achieved by flushing the apparatus with dry nitrogen and evacuating it while heating the ionic liquid.

Immediately after commencement of the experiment, the following gas composition was detected downstream of the wash bottle by means of gas chromatography: 67% of $C(O)F_2$, 0.0% of HCl, 9% of $O_2$ and 24% of further reaction components. The percentage of the other components present in the gas mixture is not reduced on passage through the ionic liquid.

1.2. Use of Acetonitrile (Comparative Example)

The experimental procedure was as described under 1.1.

A crude gas mixture having the composition 47% of $C(O)F_2$, 30% of HCl, 9% of $O_2$ and 14% of further reaction components was passed at a feed rate of 0.8 mol/h through a wash bottle containing 83 g (2 mol) of acetonitrile. Immediately after commencement of the experiment, the following gas composition was detected downstream of the wash bottle by means of gas chromatography: 55% of $C(O)F_2$, 12% of HCl, 15% of $O_2$ and 18% of further reaction components.

1.3. Reconditioning of the Ionic Liquid

Since one property of ionic liquids or mixtures of ionic liquids is an imperceptible vapour pressure, a vacuum of 10 mbar or less can be applied to the laden liquid to recondition it.

The HCl-laden ionic liquid from Example 1.1. was maintained at a reduced pressure of 10 mbar for 1 hour. Gentle heating, e.g. to 40° C., while stirring accelerated the removal of the gas from an ionic liquid which is liquid at room temperature. Evacuation was continued until no more gas was given off from the ionic liquid.

Experiment 1.3 was repeated at 1 mbar and at $1^{-3}$ mbar and in each case again led to reconditioning of the ionic liquid.

Increasing the temperature to, for example, 100° C. would likewise be expected to effect desorption with reconditioning, in a shorter time.

It can easily be established whether the ionic liquid is completely reconditioned by means of a simple mass balance of the ionic liquid before and after passing gas into it.

1.4. Use of 1-ethyl-3-methylimidazolium ethylsulphate at 0° C.

As in Example 1.1, a gas mixture from the photooxidation of $CHClF_2$ which this time contained 40% of $C(O)F_2$, 32% of HCl and further reaction components was used. The crude gas was passed at a flow rate of 0.8 mol/h under slightly elevated pressure through a wash bottle (previously flushed with $N_2$) containing 115 g of EMIM ethylsulphate (made largely water-free by application of a vacuum at about 50° C.). After commencement of the introduction, the following gas composition was determined downstream of the wash bottle by means of gas chromatography: 58% of $C(O)F_2$, 0% of HCl, 42% of further reaction components which can be separated off by distillation.

1.5. Use of 1-ethyl-3-methylimidazolium trifluoromethane-sulphonate ("EMIM triflate") at Room Temperature A gas mixture which had once again been obtained by photooxidation of $CHClF_2$ and contained 40% of $C(O)F_2$, 32% of HCl and further reaction components was used. It was passed at a flow rate of 0.8 mol/h under slightly elevated pressure through a wash bottle (again flushed with $N_2$) containing 100 g (0.38 mol) of EMIM triflate (made largely water-free by application of a vacuum at about 50° C.). After commencement of the experiment, the following gas composition was detected downstream of the wash bottle by means of gas chromatography: 53% of $C(O)F_2$, 5% of HCl, 42% of further reaction components.

The HCl content can be reduced further by further contacting with EMIM triflate.

1.6. Use of 1-ethyl-3-methylimidazolium toluenesulphonate ("L-MIM tosylate") at 60° C.

The reaction mixture used in 1.5. was, after drying of the apparatus by means of $N_2$ and application of vacuum to the ionic liquid at 100° C., passed through 100 g (0.35 mol) of EMIM tosylate. After commencement of the experiment, the following gas composition was detected downstream of the wash bottle bye means of gas chromatography: 56% of $C(O)F_2$, 0% of HCl, 44% of further reaction components.

1.7. Use of a Mixture of 1-ethyl-3-methylimidazolium trifluormethanesulphonate and 1-ethyl-3-methylimidazolium toluenesulphonate at 0° C.

EMIM triflate and EMIM tosylate were used in a molar ratio of 1:1 and any water was removed as described above. This time, a crude gas mixture containing 41% of $C(O)F_2$, 32% of HCl and further reaction components from the photooxidation of $CHClF_2$ was used. The flow rate was once again 0.8 mol/h and the total amount of ionic liquid was 100 g. After commencement of the experiment, the following gas composition was detected downstream of the wash bottle by means of gas chromatography: 63% of $C(O)F_2$, 2% of HCl, 35% of further reaction components.

In this experiment, too, the HCl content can be reduced further by renewed contacting with the mixture of the ionic liquids.

EXAMPLE 2

Separation of HCl from $PF_5$ by Means of EMIM Triflate

A test mixture comprising 56% of $PF_5$ and 44% of HCl was produced by condensation of appropriate amounts of $PF_5$ and HCl. This mixture was passed at a flow rate of 0.8 mol/h through a wash bottle containing 100 g of EMIM triflate at room temperature for 15 minutes. During this time, the ionic liquid became laden with HCl. A desorption was then carried out by applying a vacuum of 1 mbar at 100° C. for 30 minutes.

Since $PF_5$ is difficult to detect by gas chromatography (it reacts with the $SiO_2$ of the column), the following procedure was employed: the offgas stream loom the desorption was passed through a gas wash bottle containing 100 g of 0.1N NaOH solution (Titrinorm, VWR). Ion chromatography of the acidic scrub solution obtained indicated a ratio of chloride to fluoride of 95:5. For comparison, the starting mixture (44% of HCl, balance to 100% $PF_5$) was passed through 100 g of the 0.1N NaOH solution. Ion chromatography indicated a ratio of chloride to fluoride of 60:40. This comparison demonstrates that HCl is highly preferentially absorbed by the ionic liquid compared to $PF_5$.

Complete desorption can be concluded from the mass balance of the ionic liquid before and after desorption.

EXAMPLE 3

Separation of Hydrogen Fluoride (HF) and Hydrogen Chloride (HCl) from Trifluoracetyl Fluoride (TFAF) by Means of EMIM Trifluoromethane-Sulphonate Trifluoroacetyl chloride (TFAC) was stirred with hydrogen fluoride (HF) overnight in an autoclave at 50° C. The resulting mixture of TFAF and HCl and also unreacted TFAC and HF was passed through 100 g of EMIM triflate. The composition of the gas mixture before passage through the ionic liquid was determined by gas chromatography (56% of TFAF, 34% of HCl, 7% of TFAC). HF present in the gas mixture was detected qualitatively by observation of etched surfaces of glass before passage through the ionic liquid.

After passage through the ionic liquid, the following composition of the gas mixture was determined by gas chromatography: 86% of TFAF, 2% of HCl, 11% of TFAC. Analysis of the laden ionic liquid for halide ions found not only the chloride anions to be expected but also fluoride anions. These ions were not present in the unladen ionic liquid; furthermore, the fluoride value found is significantly higher than can be obtained, for example, by hydrolysis of TFAF by traces of moisture in the ionic liquid.

It was also found that the gas mixture leaving the ionic liquid no longer etched glass surfaces.

The invention claimed is:

1. A process for separating HCl and/or HF from a gas mixture comprising HCl and/or HF and one or more other gaseous constituents selected from the group consisting of carboxylic acid fluoride, $C(O)F_2$, and $PF_5$, comprising the step of contacting said gas mixture with one or more ionic liquids which sorb HCl and/or HF more strongly than carboxylic acid fluoride, $C(O)F_2$, and $PF_5$.

2. The process according to claim 1, wherein said gas mixture comprises $C(O)F_2$ and HCl, wherein said one or more ionic liquids sorbs HCl more strongly than $C(O)F_2$, and wherein said contacting results in said gas mixture being depleted in HCl, further comprising the step of isolating said HCl-depleted gas mixture.

3. The process according to claim 1, wherein said gas mixture comprises $PF_5$ and HCl, wherein said one or more ionic liquids sorbs HCl more strongly than $PF_5$, and wherein said contacting results in a gas mixture being depleted in HCl, further comprising the step of isolating said HCl-depleted gas mixture.

4. The process according to claim 1, wherein said one or more ionic liquids comprises a cation, wherein said cation comprises at least one nitrogen atom.

5. The process according to claim 1, wherein said one or more ionic liquids comprises an anion, wherein said anion has an $E_T(30)$ value of more than 20 and is capable of coordination.

6. The process according to claim 1, wherein said one or more ionic liquids comprises an anion, wherein said anion is a sulphonate, a sulphonamide, or an ester anion of a polybasic acid.

7. The process according to claim 1, wherein said one or more ionic liquids comprises an anion, wherein said anion is a monoalkylsulphate anion, monoarylsulphate anion, or an esterified phosphate or phosphonate anion, wherein said alkyl, aryl or ester groups are optionally substituted by one or more halogen atoms.

8. The process according to claim 7, wherein said anion is a mono-C1- to mono-C12-alkylsulphate.

9. The process according to claim 7, wherein said one or more ionic liquids comprises p-tosylate, m-tosylate, o-tosylate, and/or triflate anions.

10. The process according to claim 9, wherein said one or more ionic liquids comprises a mixture of at least two ionic liquids comprising p-tosylate, o-tosylate, and/or m-tosylate anions; or a mixture of one or more ionic liquids comprising p-tosylate, o-tosylate, or m-tosylate anions with at least one ionic liquid comprising a different anion.

11. The process according to claim 4, wherein said cation is selected from the group consisting of imidazolium, imidazolinium, pyrazolium, oxatriazolium, thiatriazolium, pyridinium, pyradizinium, pyrimidinium, and pyrazinium.

12. The process according to claim 11, wherein said cation is imidazolium, wherein said imidazolium is mono-, di-, or tri-substituted with substituents containing up to 24 carbon atoms, wherein said substituents are substituted or unsubstituted.

13. The process according to claim 12, wherein said cation is 1,3-dimethylimidazolium, 1-ethyl-3-methylimidazolium, 1-propyl-3-methylimidazolium, or 1-n-butyl-3-methylimidazolium.

14. The process according to claim 4, wherein said one or more ionic liquids is selected from the group consisting of 1-ethyl-3-methylimidazolium ethylsulphate, 1-ethyl-3-methylimidazolium tosylate, 1-ethyl-3-methylimidazolium triflate, and mixtures thereof.

15. The process according to claim 1, wherein said gas mixture is passed through said one or more ionic liquids.

16. The process according to claim 8, wherein said one or more ionic liquids is present in immobilised form.

17. The process according to claim 1, wherein said contacting is carried out at a temperature in the range of from 10° C. to 80° C. and at a pressure of from 1 bar to 10 bar (abs).

18. The process according to claim 1, further comprising the steps of desorbing gas mixture constituents sorbed in the ionic liquid as a result of said contacting step, followed by recovering said one or more ionic liquids and/or isolating the desorbed constituents.

19. The process according to claim 18, wherein said desorption step is effected by reducing the pressure on, increasing the temperature of, and/or passing an inert gas through the ionic liquid.

20. The process according to claim 1, wherein said mixture comprises mixtures resulting from photochemical oxidations of $CHClF_2$; mixtures resulting from fluorination reactions of phosphorus-chlorine compounds with HF; or mixtures resulting from the preparation of carboxylic acid fluorides, wherein said carboxylic acid fluorides are gaseous at 25° C. and 1 bar (abs.).

21. The process according to claim 1, wherein said process is carried out batchwise or continuously.

22. A process for separating HCl and optionally HF from a gas mixture comprising carboxylic acid fluoride, HCl, and optionally HF comprising the steps of (1) contacting said gas mixture with one or more ionic liquids which sorb carboxylic acid fluoride, HCl, and HF to differing degrees, wherein said contacting results in the gas mixture being depleted in HCl and optionally HF, and (2) isolating said HCl- and optionally HF-depleted gas mixture.

23. The process according to claim 22, wherein said gas mixture additionally comprises HF, and wherein said contacting results in a gas mixture being depleted in HCl and HF.

24. The process according to claim 22, wherein said carboxylic acid fluoride is $CH_3C(O)F$, $CHF_2C(O)F$, $CF_3C(O)F$, or $C_2F_5C(O)F$.

* * * * *